United States Patent [19]

Angevine et al.

[11] 4,382,851
[45] May 10, 1983

[54] METHYLATION PROCESS

[75] Inventors: Philip J. Angevine, West Deptford; Stuart S. Shih, Cherry Hill, both of N.J.

[73] Assignee: Mobil Oil Corporation, New York, N.Y.

[21] Appl. No.: 331,116

[22] Filed: Dec. 16, 1981

[51] Int. Cl.³ .............................................. C07C 3/52
[52] U.S. Cl. ...................................... 208/49; 208/46; 208/134; 585/467; 585/468
[58] Field of Search ................ 585/467, 468; 208/46, 208/133, 134, 49

[56] References Cited

U.S. PATENT DOCUMENTS 2,409,080 10/1946 Thacher et al. ...................... 585/454
3,718,704 2/1973 Chapman et al. .................... 546/181
4,086,289 4/1978 Seitzer ................................. 585/454

Primary Examiner—Delbert E. Gantz
Assistant Examiner—A. Pal
Attorney, Agent, or Firm—Charles A. Huggett; Michael G. Gilman; Charles J. Speciale

[57] ABSTRACT

Methylation of coal-derived liquids and other polynuclear aromatic distillate feed stocks for improving distillate fuel quality is achieved by contacting the feed stock with hydrogen sulfide and carbon monoxide over conventional sulfur-resistant hydrotreating catalysts. The resultant product comprises methylated aromatic and hydroaromatic molecules of increased diesel quality. Further hydrogenating of the methylated hydrocarbons further increases the cetane number of the methylated product. A major product of the methylation reaction is elemental sulfur.

11 Claims, 3 Drawing Figures

METHYLATION PROCESS

BACKGROUND OF THE INVENTION

1. Field of the Invention

This invention relates to the preparation of methylated aromatic and hydroaromatic compounds, particularly to the preparation of methylated polynucleated aromatics or hydroaromatics. This invention also relates to a process for upgrading highly aromatic feedstocks such as coal-derived, distillate hydrocarbons and certain highly aromatic petroleum-derived hydrocarbons such as FCC clarified slurry oil, TCC syntower bottoms and heavy coker gas oil.

2. Description of the Prior Art

U.S. Pat. No. 2,409,080 discloses the reaction of alkyl mercaptans or sulfides with carbocyclic compounds in the presence of a copper pyrophosphate catalyst to form alkylated cyclic hydrocarbons. Hydrogen sulfide is formed by side reactions in the U.S. Pat. No. 2,409,080 process. The patent teaches that such formed hydrogen sulfide should be removed from unreacted charge stock recovered from the reaction zone.

U.S. Pat. No. 3,718,704 teaches methylation of aromatic hydrocarbons with a carbon-oxide containing reactant gas in the presence of an oxide of a Group IB, IIB and/or VIB metal containing catalysts. The process is preferably carried out in the presence of added hydrogen.

U.S. Pat. No. 4,086,289 discloses a modification of the U.S. Pat. No. 3,718,704 process, supra., wherein the process of methylating toluene to obtain a mixture of xylenes relatively low in the meta-isomer and low in ethyl benzene content by contacting toluene with hydrogen and a carbon oxide-containing gas in the presence of a catalyst, utilizes as the catalyst zinc chromite mixed with an alkali metal exchanged molecular sieve containing a stoichiometric excess of an alkali metal carbonate.

Coal-derived liquids obtained by most direct liquefaction processes are primarily bare ring polynuclear aromatic and hydroaromatic, (i.e. partially saturated) molecules containing few alkyl side-chains. The highly condensed nature of these materials, caused by the hydrodealkylation of the high temperature liquefaction step, makes coal liquids low in cetane number and, therefore, poor components for diesel fuel. Nearly complete hydrogenation of the aromatic rings is needed to obtain high cetane quality material, but thermodynamic limitations to aromatic saturation require very high hydrogen partial pressures (greater than 3000 psi) to obtain high saturation (i.e., less than 10 weight percent aromatics) at reasonable reaction temperatures and contact times. Some petroleum-derived hydrocarbons are also primarily bare ring poly-nuclear aromatics. Examples of such hydrocarbon streams are FCC clarified slurry oil, TCC syntower bottoms, and heavy coker gas oil.

An object of the present invention is to provide an efficient method for upgrading polynuclear aromatic and hydroaromatic feed stocks. A more specific object is to produce a higher cetane quality diesel fuel at a given level of aromatic saturation by raising the hydrogen content of the fuel without direct use of molecular hydrogen. A related object is to provide a method for improving distillate fuel quality by direct methylation. A still further related object of this invention is to provide a method for improving distillate fuel quality without hydrocracking. Another object of this invention is to usefully recover hydrogen from hydrogen sulfide.

SUMMARY OF THE INVENTION

It has now been discovered that aromatic or hydroaromatic feedstocks may be methylated by reaction of hydrogen sulfide and carbon monoxide with an aromatic species, ArH, and can be expressed as follows:

$$ArH + H_2S + 2CO \rightleftharpoons Ar\text{-}CH_3 + CO_2 + S \qquad (1)$$

An aromatic molecule may also undergo multiple methylation. Further, additional hydrotreating of the methylated hydrocarbon under moderate hydrogen partial pressures improves the cetane number of the methylated distillate. It is known that diesel fuel produced from coal, particularly through coal liquefication processes, is low in cetane number. The process of the present invention produces a higher quality diesel fuel from coal-derived liquids and significantly improves the flexibility of coal liquefaction processes.

As can be seen, a major product of reaction (1) is elemental sulfur. Consequently, the process of the present invention can reduce the throughput of, or completely eliminate the need for, a Claus sulfur recovery plant. The overall reaction of the Claus process releases the hydrogen as $H_2O$:

$$H_2S + \tfrac{1}{2}O_2 \rightleftharpoons H_2O + S \qquad (2)$$

Unlike the Claus process which releases the hydrogen content of hydrogen sulfide as water, hydrogen sulfide is a valuable, hydrogen-providing reactant in the process of the present invention. The present process utilizes the hydrogen in the hydrogen sulfide for raising the hydrogen content of the fuel products. Additionally, recovery of hydrogen from hydrogen sulfide and elimination of the sulfur recovery plant will reduce synthetic fuel cost.

Besides methylating coal-derived liquids, the process of the present invention can also be extended to highly aromatic petroleum feed stocks, such as converting low value FCC clarified slurry oil or coker gas oil to high value diesel blending stock.

DETAILED DESCRIPTION OF THE INVENTION

Gibbs free energy calculations as well as calculation of equilibrium constants show that methylation and hydrogenation with $H_2S/CO$ are strongly thermodynamically favored. For example, the logarithm of the equilibrium constant is plotted as a function of temperature in FIG. 3 for the methylation of benzene:

$$2C_6H_6 + 2H_2S + 4CO \rightleftharpoons C_6H_5CH_3 + 2CO_2 + S_2 \qquad (3)$$

Figure 3:
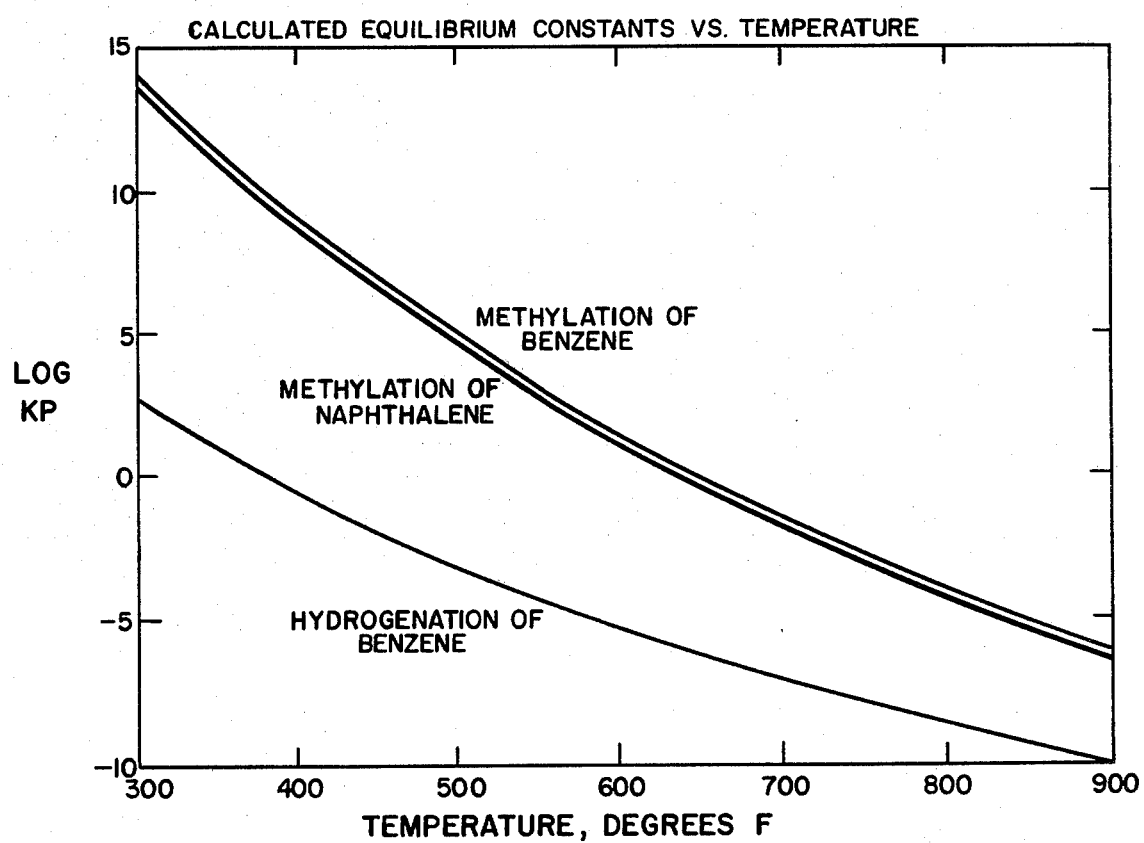
FIG. 3 shows calculated equilibrium constants as a function of temperature in the methylation of naphthalene and benzene.

Additionally, the logarithm of the equilibrium constant for the hydrogenation of benzene is plotted as a function of temperature in FIG. 3:

$$C_6H_6 + 3H_2S + 3CO \rightleftharpoons C_6H_{12} + 3COS \quad (4)$$

Hydrogenation is not an undesirable reaction because it also results in an increased hydrogen content. In terms of product quality, however, the methylation reaction is more desirable than the hydrogenation reaction because the methylated aromatic species can be further hydrogenated by conventional processes. The selectivity between methylation and hydrogenation can be controlled by choice of catalyst as well as process conditions. As shown in FIG. 3, at atmospheric pressure the methylation of benzene, cited as a representative reactant, is thermodynamically more favorable than hydrogenation throughout the temperature range of 300°-900° F. Moreover, the methylation is favorable (i.e., log $Kp > 0$) at temperatures below 675° F.

Other hydrogen-consuming reactions such as denitrogenation, desulfurization, and deoxygenation are expected to take place. Again, these side reactions are also desirable reactions.

It should be noted that the methanation reaction is thermodynamically unfavorable (i.e., $-56.0 > \log Kp > -36.8$) for a temperature range of 0°-900° F.

$$2CO + 4H_2S \rightleftharpoons 2CH_4 + 2S_2 + O_2 \quad (5)$$

Accordingly, from FIG. 3 it can be readily seen that benzene methylation by reaction with $H_2S$ and CO is more favorable than benzene hydrogenation by addition of the same reactants and greater than the methanation between $H_2S$ and CO. The methylation of higher aromatics is also favorable. For example, naphthalene can be methylated to form 2-methyl-naphthlene by the following reaction:

$$2C_{10}H_8 + H_2S + 4CO \rightleftharpoons 2C_{11}H_{10} + 2CO_2 + S_2 \quad (6)$$

A plot of calculated equilibrium constants as a function of temperature for the methylation of naphthalene is also shown in FIG. 3. The plot shows that the methylation of naphthalene is similarily favored.

The term "aromatic" is used herein to denote substituted and unsubstituted mono- and poly-nuclear ring compounds. Compounds of the benzene series as well as compounds of an aromatic character which are or contain a heterocyclic ring are examples of aromatic compounds. These substituted aromatic compounds must, however, contain at least 1 hydrogen attached to the aromatic nucleus. The aromatic rings may be substituted with alkyl groups, aryl groups, alkaryl groups, hydroxy groups, amine groups, alkoxy groups, aryloxy groups, cycloalkyl groups, halide groups, and mixtures of these groups and other radicals which do not prevent the desired reaction.

Suitable aromatic hydrocarbons include benzene, naphthalene, biphenyl, anthracene, naphthacene, chrysene, pyrene, triphenylene, pentacene, picene, perylene, coronene, and phenanthrene.

The term "hydroaromatic" is used herein to denote partially saturated cyclic or polycyclic hydrocarbons. The hydroaromatics may be mono- or poly-nuclear and also may be mono- or poly-substituted.

Generally, the alkyl groups which can be present as substituents on the aromatic or hydroaromatic compounds contain from 1 to 22 carbon atoms and preferably from about 1 to 8 carbon atoms and preferably from about 1 to 8 carbon atoms and more preferably from about 1 to 4 carbon atoms.

Some suitable aromatic compounds having heterocyclic rings wherein nitrogen is the heterocyclic atom include pyridine, alkyl substituted pyridines, furans, e.g. benzofurans and dibenzofurans, and quinolines. The thiophene class (e.g. thiophene, benzothiophene, dibenzothiophene, etc.) is examplary of aromatic compounds wherein the heterocyclic atom is sulfur.

Figure 1:
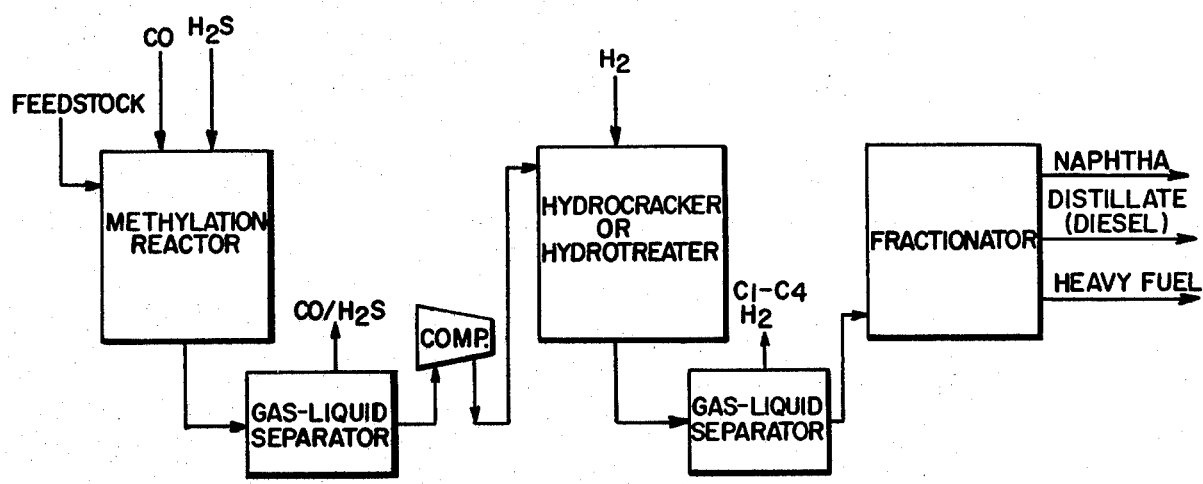
FIG. 1 is a block flow diagram of the process of this invention which comprises methylation of the feedstock followed by hydrotreating or hydrocracking.

Referring again to the drawings, FIG. 1 is a block diagram illustrating the methylation of a feed stock followed by further hydrotreating to improve the cetane value. A fractionation stage may be included after hydrocracking or hydrotreating to recover the high quality diesel distillate. The feed stock is typically a hydrogen-deficient, highly nuclear aromatic petroleum, coal-derived tar sands bitumen or shale oil hydrocarbon stream having a boiling range of about 380° to 900° F. Suitable coal-derived liquids which may be used as feed stock may be obtained as a product from any direct coal liquefication process (e.g., SRC, H-coal, EDS, Dow, etc.). Typically, a significant portion of the coal-derived liquid feed stock contains bare ring polynuclear aromatics such as naphthalene, phenanthrene, and anthracene as well as singly methylated and/or partially hydrogenated forms of naphthalene, phenanthrene, and anthracene. The feed stock enters the methylation reactor and passes downwardly over a conventionally sulfur-resistant hydrotreating catalyst, such as $Co-Mo/Al_2O_3$, cocurrently with a gas stream comprising primarily of CO and $H_2S$. The gas stream contains CO and $H_2S$ in a molar ratio of about 2:1. The methylation reaction takes place at a temperature of about 500° to about 700° F. and at pressures of about 0 to about 2000 psig. The liquid hourly space velocity (LHSV) is about 0.2 to about 10 and the gas circulation is about 100 to about 10,000 SCF/B. Preferred process conditions can be set forth as follows:

T = 550°-700° F.; P = 600-1200 psig; LHSV = 0.75-2.0; and gas circulation = 3000-6000 SCF/B.

The total effluent from the methylation reactor is passed through a high temperature flash vessel to separate the light gases (e.g., $C_1-C_4$, unreacted $H_2S$, CO, COS, etc.) from the $C_5+$ and methylated hydrocarbons which are separated in the liquid state. The methylated hydrocarbon stream is then upgraded by hydrogenation in a hydrocracker or hydrotreater to increase diesel quality, to decrease smoke point, and/or to increase heating value. The hydrocarbon stream from the gas-liquid separator is vaporized and pressurized to about 1000 psig in the compressor. The higher pressures are necessary to achieve the desired aromatic saturation during hydrogenation. In the hydrogenator, the pressurized methylated hydrocarbon stream is passed cocurrently with a high purity hydrogen gas (greater than 80%) downwardly over a fixed bed containing a sulfur-resistant hydrogenation catalyst such as $NiMo/Al_2O_3$, $Ni-W/Al_2O_3$, $Co-Mo/Al_2O_3$, etc. Process parameters in the hydrogenator include a temperature range of about 550° to about 800° F., a pressure of about 1000 to about 3000 psig, LHSV equal to about 0.5 to about 10, and a hydrogen circulation equal to about 1000 to about 10,000 SCF/B. A more preferred range of process parameters include; T = to about 675°-775° F.; P = to about 2000-25000 psig; LHSV = to about 1.0 to about 3.0; and a hydrogen circulation to about 3000-6000 SCF/B. The hydrogenation conditions are selected such that most of the carbon bonds are non-aromatic (e.g., saturated) and that the aromatics comprise less than 50% by weight of the products stream. Representatives of the product molecules leaving the hydrogenator include 1-methyl tetralin, 1,6-dimethyltetralin, 2-methyl decalin, and 1,6-dimethyl decalin. The total effluent from the hydrogenator is then passed through a second gas-liquid separation operation which includes cooling and a flash separation to remove the light hydrocarbons such as the $C_1$-$C_4$ hydrocarbons, the unconverted hydrogen, and any trace product such as $H_2S$ or $NH_3$. These contaminants as a whole make up no more than 20 mole percent of the effluent stream. The contaminant gases which are separated from the effluent stream can be purified using conventional technology. The liquid hydrocarbon product is a strongly hydrogenated distillate range material which, if required, is directed to the fractionator wherein the lighter products from the hydrogenating operation, such as naphtha produced during hydrocracking, can be separated and used for reforming while the major product within the distillate diesel range is recovered.

As indicated in FIG. 1, the hydrogenation of the methylated feed stock can comprise either hydrocracking or hydrotreating. The hydrocracking operation is useful when the feed stock comprises hydrocarbon materials having a relatively wide nominal boiling range which is typical of coal-derived liquids which can have a boiling point as high as 800° or 900° F. The hydrocracker which is useful in the present invention will not ordinarily operate as a conventional hydrocracker which has the objective of producing gasoline. The objective of the present invention for hydrocracking is to produce a mixed hydrocarbon, and one that will produce a distillate range material having a nominal boiling point range typical of a good quality diesel distillate. The naphtha which is produced in the hydrocracking process is merely an artifact of the overcracking in the hydrocracker. The broad process parameters in operating the hydrocracker are in the same range as used in the hydrotreater. Typical hydrocrackers operate initially at about 550° F. Coal-derived liquids, however, contain significant portions of nitrogen such that any hydrocracking operation will of necessity be more severe and require slightly larger start up temperatures. Hydrotreating is used merely to increase the hydrogen content of the methylated feed stock. Typically, the feed stock would have a nominal boiling point range which is relatively narrow in which the end point is about 650° to about 700° F. The purpose of the hydrotreating is merely to saturate additional aromatic carbons and lower the aromatic carbon content. The effluent from the hydrotreater is primarily a distillate useful for diesel fuel and would be substantially devoid of naphtha content.

Figure 2:
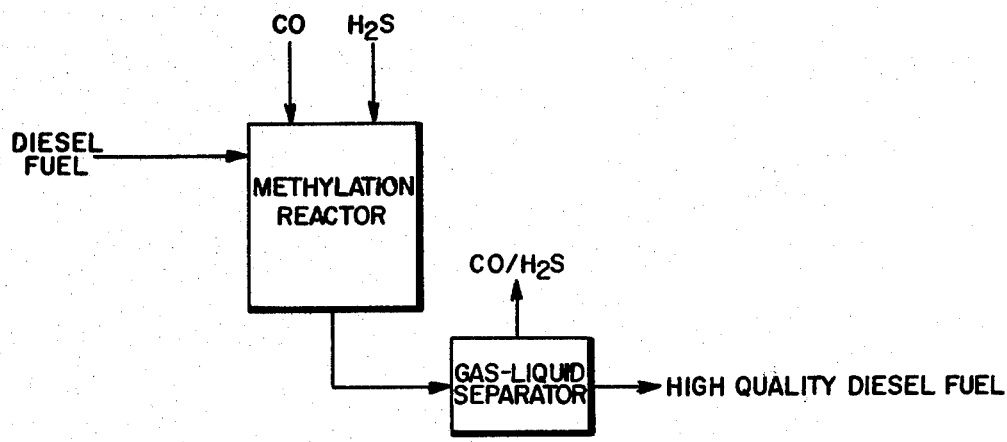
FIG. 2 is a block flow diagram of the process of this invention which comprises improving distillate fuel quality by direct methylation.

In FIG. 2, a more simplified methylation process is diagrammed. The methylation process referred to in FIG. 2 is useful in methylating distillate fuels which are to some degree hydrogenated but which still contain substantial quantities of bare ring aromatics such as hydrogenated anthracene or phenanthrene and like molecules. The nominal boiling point range of the feed stock will be about 380° to about 650° F. and occasionally a slightly higher end point. The feed stock utilized in the process illustrated by FIG. 2 is one that may be derived from SRC or solvent refined coal process which is a non-catalytic operation and has not included a significant hydrogenation operation. The feed stock may also be a product from an H-coal operation in which the feed stock is relatively more hydrogenated. Therefore, it is desirable only to increase by a relatively small degree the alkylation and hydrogen content of the feed stock. This can be done simply by methylation and foregoing the downstream hydrogenation step. For illustration purposes, the feed stock shown is diesel fuel, but it should be understood that the feed stock is of low quality and has a relatively low cetane number.

The process parameters of the methylation reactor are equivalent to that described previously. Accordingly, the low grade fuel is passed under pressure into the methylation reactor co-currently with the hydrogen sulfide and carbon monoxide gases, the streams passing down the reactor through the catalytic bed in a trickle flow operation wherein much of the diesel fuel remains in the liquid phase. The total effluent product from the methylation reactor is cooled, undergoes a vapor-liquid separation, the unconverted hydrogen sulfide and carbon monoxide are purified for recycle and the remaining products removed including elemental sulfur, carbon dioxide and possibly minute quantities of COS. The liquid which is recovered is a high quality diesel fuel with increased cetane number. It may be desired to further fractionate the diesel fuel to remove small amounts of distillate which do not meet the specification of diesel.

For a given feed stock, the criteria for determining whether the downstream hydrogenation operation as shown in FIG. 1 is required or whether a simple methylation is needed is the aromatic carbon content. In order to produce a high quality diesel fuel, it has been found that in processing feed stocks which contain more than about ⅛ to about 40% by weight aromatic carbons, the hydrotreating or hydrocracking step should be included downstream from the methylation reactor. For example, octahydroanthracene contains 8 non-aromatic carbons and 6 aromatic carbons. This material would be sufficiently hydrogenated so as to not require any subsequent hydrocracking or hydrotreating operation. Methylation of such material would produce an acceptable diesel quality fuel. As previously discussed, the criteria for determining which hydrogenation process to utilize will depend upon the boiling point range of the highly aromatic feed stock.

To illustrate the advantages of methylating bare ring aromatic compounds and raising the hydrogen content and thus increase cetane value, Table 1 provides a comparison between bare ring compounds and methylated derivitives thereof.

TABLE I

| Comparative Cetane Values | |
|---|---|
| Molecule | Calculated Cetane Index* |
| Tetralin | −10.3 |
| 1-Methyltetralin | − 4.9 |
| 1,6-Dimethyltetralin | 6.5 |
| Decalin | 9 |
| 2-Methyldecalin | 23 |
| 1,6-Dimethyldecalin | 34 |

*The calculated cetane index herein set forth determined by ECS-1 meter basis-ASTM method D613, based on the ASTM classification of diesel fuel oils D975.

As can be readily determined from Table I, methylation and the increased hydrogen content of the methylated hydrocarbons greatly improves the cetane index of the bare ring molecules. The dimethyl substituted tetralin has a cetane advantage of 16.8 over the bare ring molecule. The dimethyl substituted decalin has a cetane advantage of 25 over the bare ring molecule. Accordingly the methylation and, if required, the further hydrogenation of primarily bare ring feed stocks can greatly improve the quality of these materials and make them useful for good quality diesel distillates, such as diesel fuel, jet fuel, kerosene, etc. Although the relative demand for high cetane quality distillate has increased, the quality of hydrocarbon resources is declining. The methylation process of the present invention enables the inclusion of previously low quality feed stocks as part of the distillate pool. Additionally, the process of the present invention reduces or eliminates the need for the Claus sulfur recovery plant and in addition uses the hydrogen content of hydrogen sulfide.

It is to be understood that the foregoing description is merely illustrative of the preferred embodiments of the invention of which many variations may be made by those skilled in the art within the scope of the following claims without departing from the spirit thereof.

What is claimed is:

1. A process for producing methylated aromatic or hydroaromatic compounds which comprises contacting an aromatic or hydroaromatic feed stock with hydrogen sulfide and carbon monoxide, said hydrogen sulfide and carbon monoxide being provided in sufficient amounts to react with the aromatic and hydroaromatic compounds in said feedstock to produce said methylated compounds and elemental sulfur.

2. The process of claim 1 wherein said feed stock is contacted with hydrogen sulfide and carbon monoxide in the presence of a conventional sulfur-resistant hydrotreating catalyst.

3. The process of claim 2 wherein said catalyst is selected from the group of consisting of Co-Mo, Ni-Mo and Ni-W supported on a porous alumina.

4. The process of claim 3 wherein said feed stock is contacted with hydrogen sulfide and carbon monoxide at a temperature within the range of about 500° to about 750° F. and a pressure within the range of about 0 to about 2000 psig, and a hydrocarbon liquid hourly space velocity of 0.2 to 10.0.

5. The process of claim 1 wherein said aromatic or hydroaromatic feed stock is a component of a petroleum, coal-derived liquid, tar sands bitumen or shale oil hydrocarbon stream.

6. The process of claim 2 in which said methylated compounds are further hydrogenated to increase cetane value.

7. The process of claim 6 wherein said methylated compounds are further hydrogenated by hydrotreating or hydrocracking.

8. The process of claim 2 wherein said feed stock is a coal-derived distillate having a nominal boiling range characteristic of diesel fuel.

9. The process of claim 2 in which said feed stock is a distillable fraction having a nominal boiling range characteristic of jet fuel or kerosene.

10. The process of claim 2 wherein said feed stock is a petroleum or coal-derived liquid reformate.

11. The process of claim 6 wherein said feed stock has an aromatic carbon content greater than about ⅓ by weight of said feed stock.

* * * * *